US00PP23991P2

(12) United States Plant Patent
Hartman

(10) Patent No.: US PP23,991 P2
(45) Date of Patent: Oct. 15, 2013

(54) ***CALADIUM* PLANT NAMED 'CREAMSICKLE'**

(50) Latin Name: *Caladium×hortulanum*
Varietal Denomination: Creamsickle

(76) Inventor: Robert Dale Hartman, Lake Placid, FL (US)

( * ) Notice: Subject to any disclaimer, the term of this patent is extended or adjusted under 35 U.S.C. 154(b) by 130 days.

(21) Appl. No.: 13/374,465

(22) Filed: Dec. 29, 2011

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — June Hwu
(74) *Attorney, Agent, or Firm* — C. A. Whealy

(57) ABSTRACT

A new and distinct cultivar of *Caladium* plant named 'Creamsickle', characterized by its upright plant habit; tall plant size; uniform plant habit; vigorous and dense growth habit; fancy-type leaves with greyed green-colored venation, greyed green and greyed purple-colored interveinal areas interspersed with dark-green sectors and surrounded by dark green-colored borders; and good landscape performance.

4 Drawing Sheets

Botanical designation: *Caladium×hortulanum.*
Cultivar denomination: 'CREAMSICKLE'.

BACKGROUND OF THE INVENTION

The present invention relates to a new and distinct cultivar of *Caladium* plant, botanically known as *Caladium×hortulanum*, commercially referred to as a fancy leaf-type *Caladium* and hereinafter referred to by the name 'Creamsickle'.

The objective of the Inventor's breeding program is to create new *Caladium* plants that have uniform plant habit, exceptional container and garden performance and attractive foliage coloration.

The new *Caladium* plant originated from a cross-pollination made by the Inventor on Apr. 15, 2007, in Avon Park, Fla. of *Caladium×hortulanum* 'Aaron', not patented, as the female, or seed, parent with *Caladium×hortulanum* 'Twist N' Shout', not patented, as the male, or pollen, parent. The new *Caladium* plant was discovered and selected by the Inventor as a single plant within the progeny of the stated cross-pollination in a controlled outdoor nursery environment in Zolfo Springs, Fla. on Sep. 15, 2008.

Asexual reproduction of the new *Caladium* plant by 'chipping' the tubers (cutting the tuber into segments each segment containing an axillary bud and tuber cortical tissue) in a controlled outdoor nursery environment in Lake Placid, Fla. since Apr. 15, 2009 has shown that the unique features of this new *Caladium* plant are stable and reproduced true to type in successive generations of asexual reproduction.

SUMMARY OF THE INVENTION

Plants of the new *Caladium* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Creamsickle'.

These characteristics in combination distinguish 'Creamsickle' as a new and distinct *Caladium* plant:

1. Upright plant habit; tall plant size.
2. Uniform plant habit.
3. Vigorous and dense growth habit.
4. Fancy-type leaves with greyed green-colored venation, greyed green and greyed purple-colored interveinal areas interspersed with dark-green sectors and surrounded by dark green-colored borders.
5. Good landscape performance.

Plants of the new *Caladium* differ primarily from plants of the female parent, 'Aaron', in the following characteristics:

1. Plants of the new *Caladium* are taller than plants of 'Aaron'.
2. Plants of the new *Caladium* grow faster than plants of 'Aaron'.
3. Leaves of plants of the *Caladium* are more undulating than leaves of plants of 'Aaron'.
4. Plants of the new *Caladium* and 'Aaron' differ in leaf coloration as leaves of plants of 'Aaron' have white-colored venation and radiating interveinal areas surrounded with green-colored margins.

Plants of the new *Caladium* differ primarily from plants of the male parent, 'Twist N' Shout', in the following characteristics:

1. Plants of the new *Caladium* are taller than plants of 'Twist N' Shout'.
2. Plants of the new *Caladium* grow faster than plants of 'Twist N' Shout'.
3. Plants of the new *Caladium* and 'Twist N' Shout' differ in leaf coloration as leaves of plants of 'Twist N' Shout' have red orange-colored venation and interveinal areas with narrow green-colored margins.

Plants of the new *Caladium* can be compared to plants of *Caladium* 'Roselight', not patented. In side-by-side comparisons conducted in Avon Park, Fla., plants of the new *Caladium* differed primarily from plants of 'Roselight' in the following characteristics:

1. Plants of the new *Caladium* were taller than plants of 'Roselight'.

2. Plants of the new *Caladium* grew faster than plants of 'Roselight'.
3. Plants of the new *Caladium* and 'Roselight' differed in leaf coloration as leaves of plants of 'Roselight' were medium green in color with variable coalescing rose pink spots and blotches and green-colored venation and borders.

Plants of the new *Caladium* can also be compared to plants of *Caladium* 'Carolyn Whorton', not patented. In side-by-side comparisons conducted in Avon Park, Fla., plants of the new *Caladium* differed primarily from plants of 'Carolyn Whorton' in the following characteristics:

1. Plants of the new *Caladium* were taller than plants of 'Carolyn Whorton'.
2. Plants of the new *Caladium* grew faster than plants of 'Carolyn Whorton'.
3. Plants of the new *Caladium* and 'Carolyn Whorton' differed in leaf coloration as leaves of plants of 'Carolyn Whorton' had deep rose red-colored venation with pink-colored blotches and green-colored borders.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Creamsickle' grown in a 15-cm container in a shadehouse.

The photograph at the top of the second sheet is a side perspective view of typical plants of 'Creamsickle' grown in an outdoor nursery.

The photograph at the bottom of the second sheet is a close-up view of typical freshly-harvested tubers and roots of 'Creamsickle'.

The photograph on the third sheet is a comparison view of typical plants of 'Creamsickle' grown in 15-cm containers, the plant on the right has not had its tuber de-eyed and the plant on the left has had its tuber de-eyed prior to planting.

The photograph at the top of the fourth sheet is a comparison view of typical potted plants of the female parent, 'Aaron' (left), 'Creamsickle' (center) and the male parent, 'Twist N' Shout' (right).

The photograph at the bottom of the fourth sheet is a comparison view of typical potted plants of 'Roselight' (left), 'Creamsickle' (center) and 'Carolyn Whorton' (right).

DETAILED BOTANICAL DESCRIPTION

The aforementioned photographs and following observations and measurements describe plants grown during the spring in 15-cm containers in Avon Park, Fla. in a polypropylene-covered shadehouse (30% shade) and plants grown during the autumn in ground beds in an outdoor nursery in Zolfo Springs, Fla. All plants were grown under environmental conditions and cultural practices which approximate those generally used in commercial shadehouse and outdoor nursery *Caladium* production. During the production of the plants, day temperatures ranged from about 29° C. to 33° C. (shadehouse) or 29° C. to 35° C. (outdoor nursery), night temperatures ranged from about 22° C. to 25° C. (shadehouse) or 23° C. to 26° C. (outdoor nursery) and light levels were about 8,000 foot-candles (shadehouse) or 10,000 to 12,000 foot-candles (outdoor nursery). Plants grown in the shadehouse were six weeks old when the photographs and the detailed description were taken. Plants grown in the outdoor nursery were seven months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Creamsickle'.

Parentage:

*Female, or seed, parent.*—*Caladium×hortulanum* 'Aaron', not patented.

*Male, or pollen, parent.*—*Caladium×hortulanum* 'Twist N' Shout', not patented.

Propagation:

*Type.*—By "chipping" the tubers.

*Time to initiate roots, summer.*—About seven to ten days at 32° C.

*Time to initiate roots, winter.*—About two to three weeks at 24° C.

*Tuber description* (*outdoor nursery-grown plants*).—Appearance: Multi-segmented; individual segments elliptic in shape. Height: About 3.4 cm. Diameter: About 5.6 cm. Texture: Thick and starchy; somewhat brittle. Color: Epidermis, freshly harvested, more brown than 199A to 199B and N199B; epidermis, dried tuber, close to 200A to 200B; interior, close to 155D; axillary buds, close to 155B. Root description: Thick, fleshy contractile roots; color, close to 155C. Rooting habit: Few lateral branches; moderately dense.

Plant description:

*Plant type.*—Herbaceous perennial; suitable as a potted plant in containers 15-cm to 25-cm and suitable as a landscape plant in shaded areas.

*Plant and growth habit.*—Upright plant habit; tall plant size; inverted triangle; vigorous and dense growth habit; rapid growth rate; petioles and leaves arise from one or more growing points on tubers; petioles mostly upright and leaning outwardly with development.

*Plant height, from soil level to top of foliar plane, shadehouse-grown potted plants.*—About 41 cm to 49 cm.

*Plant diameter or spread, shadehouse-grown potted plants.*—About 43 cm to 50 cm.

*Number of clumps per plant, shadehouse-grown potted plants.*—About four to six from de-eyed tubers.

*Cataphylls, shadehouse-grown potted plants.*—Length: About 8 cm to 17 cm. Width: About 1.1 cm to 2 cm. Shape: Deltoid to ligulate. Apex: Acute to emarginate. Base: Sheathing the stem. Color, outer surface: Close to 147C to 147D variably stippled and tessellated with close to 147A to 147B and faintly tinged with close to 199A; with development, color becoming closer to 199A stained with close to N186C. Color, inner surface: Close to 195B streaked and stippled with close to 147B.

Foliage description:

*Length, shadehouse-grown potted plants.*—About 16 cm to 23 cm.

*Width, shadehouse-grown potted plants* (*flattened*).—About 12.5 cm to 16.5 cm.

*Shape.*—Ovate.

*Apex*.—Acuminate to acute.

*Base*.—Sagittate, peltate.

*Margin*.—Entire; broad undulations.

*Texture, upper surface*.—Smooth, glabrous.

*Texture, lower surface*.—Smooth, glabrous; glaucous.

*Venation pattern*.—Pinnate.

*Color, shadehouse-grown potted plants*.—Developing leaves, upper surface: Basal notch: Close to 187A. Midrib and primary veins: Close to 192D. Areas surrounding the primary venation: Close to 53A to 53B. Interveinal areas: Close to 53A to 53B, 183B and close to 192D; random sectors and spots, close to 147A and 192D. Borders and margins: Close to 147A. Developing leaves, lower surface: Basal notch: Close to 187A. Midrib and primary veins: Close to 147C to 147D. Areas surrounding the primary venation: Close to 187B to 187C. Interveinal areas: Close to 191A, close to 191A tinged with close to 177C to 177D, close to 177C tinged with close to 183D and close to 155C. Borders and margins: Close to 147A. Fully expanded leaves, upper surface: Basal notch: Close to 187A. Midrib: Close to 191D. Primary venation: Close to 191D, and close to 191D flecked and streaked with close to 147A. Areas surrounding the primary venation: Close to 192D. Interveinal areas: Random sectors and splotches, close to 185B, 185A and darker than 147A. Borders and margins: Close to 147A. Fully expanded leaves, lower surface: Basal notch: Close to 187A. Midrib: Close to 147D. Primary venation: Close to 147C and 147D. Areas surrounding the primary venation: Close to 155C. Interveinal areas: Close to 191A tinged with close to 171C, close to 191A, close to 189A and close to lighter than 183D. Borders and margins: Close to 191A and 189A.

*Petiole*.—Aspect: Mostly erect, slightly outwardly leaning with development; flexible. Length, shadehouse-grown potted plants: About 28.5 cm to 40 cm. Diameter, distal, shadehouse-grown potted plants: About 3 mm to 4.5 mm. Diameter, proximal, shadehouse-grown potted plants: About 8 mm to 11 mm. Color, shadehouse-grown potted plants: Close to 147C and 146C faintly tessellated with close to 147B; below the leaf/petiole junction, close to 147C. Wing length, shadehouse-grown potted plants: About 7 cm to 12 cm. Wing diameter, shadehouse-grown potted plants: About 1 cm to 1.4 cm. Wing color, shadehouse-grown potted plants, outer surface: Close to 147C to 147D variably stippled and tessellated with close to 147A and 147B and faintly tinged with close to 199A. Wing color, shadehouse-grown potted plants, inner surface: Close to 195B streaked and stippled with close to 147B.

Inflorescence description: Inflorescence initiation and development have not been observed on plants of the new *Caladium*.

Disease & pest tolerance/resistance: Plants of the new *Caladium* have been observed to have above average tolerance to *Xanthomonas* Leaf Spot and average tolerance to *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and suitable for USDA Hardiness Zones 8A to 11.

It is claimed:

1. A new and distinct *Caladium* plant named 'Creamsickle' as illustrated and described.

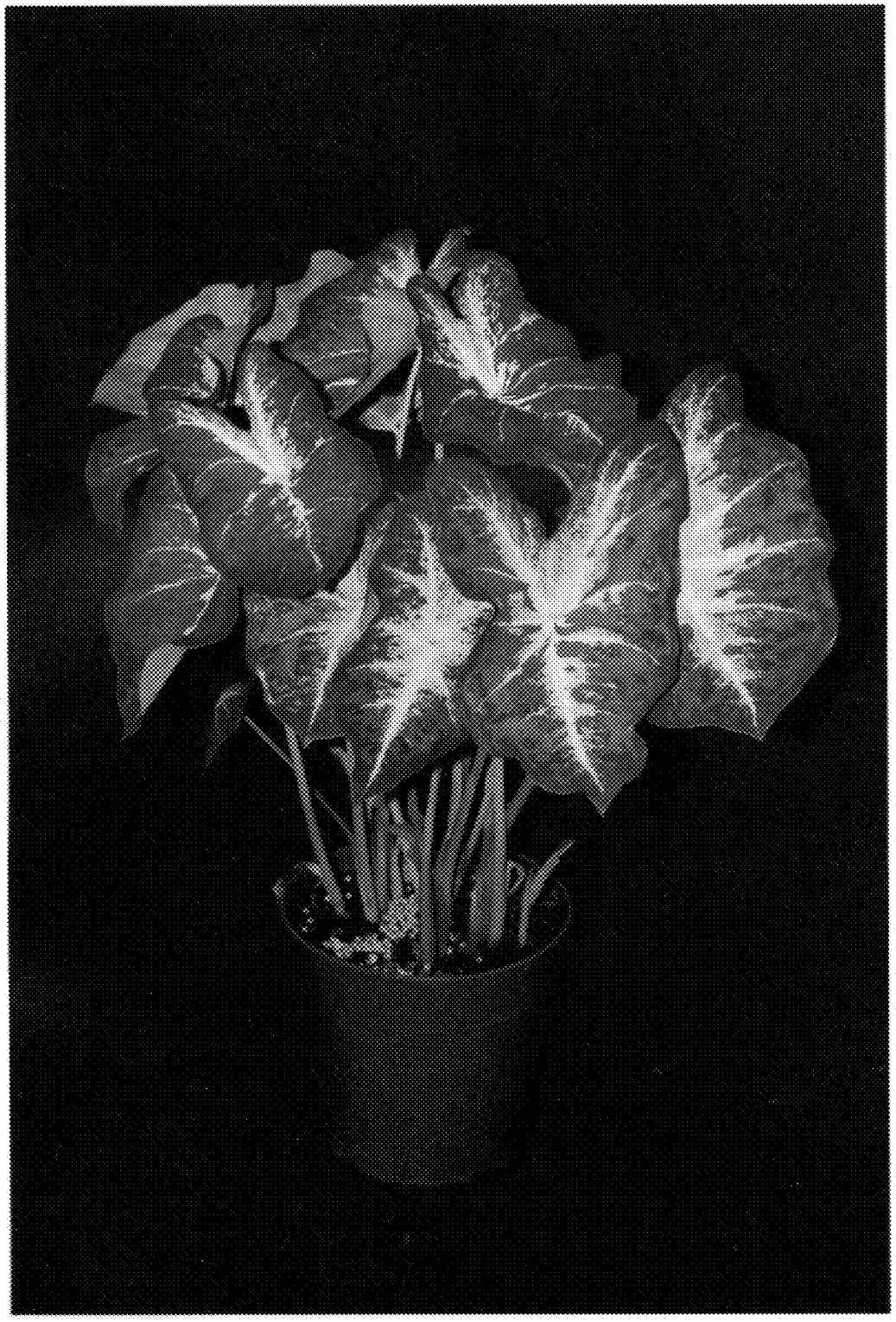

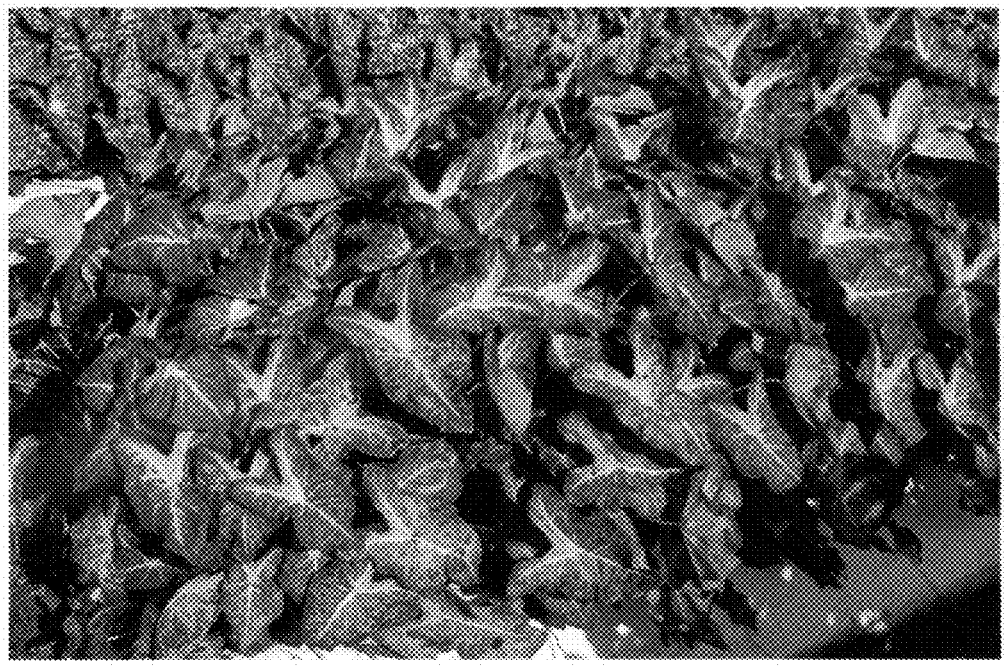
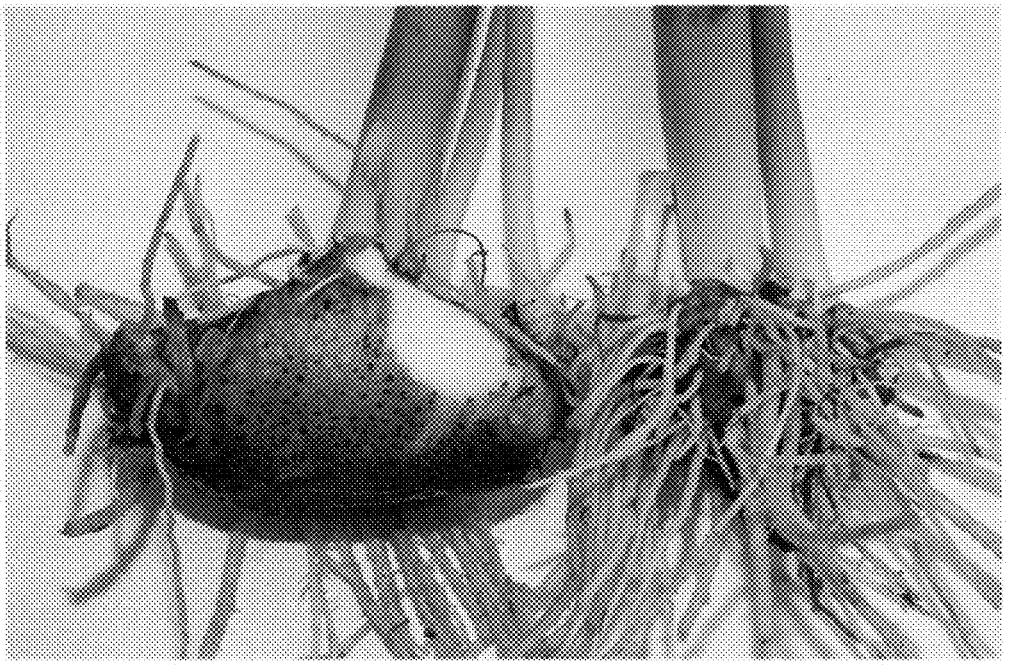

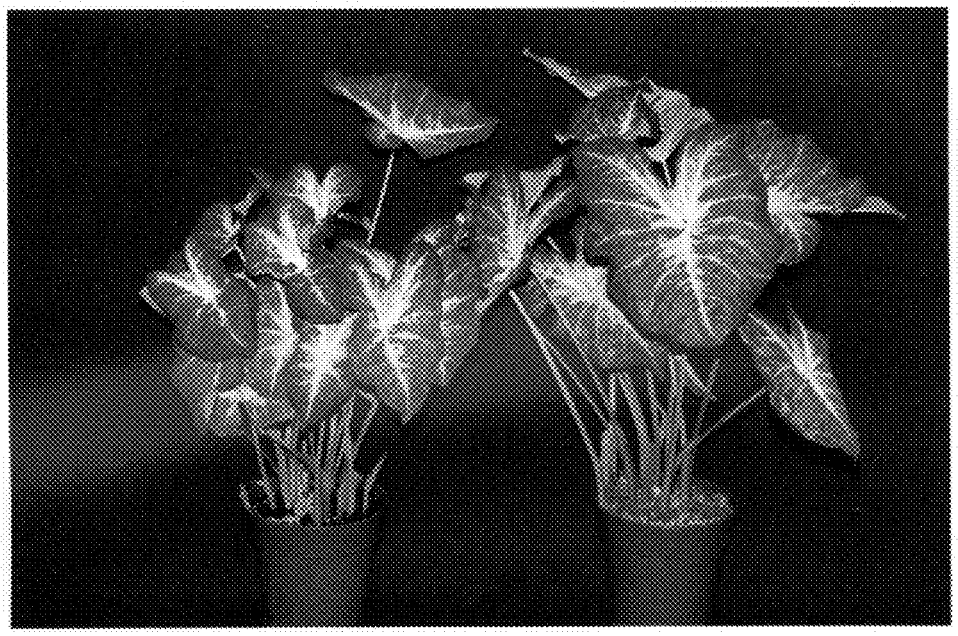

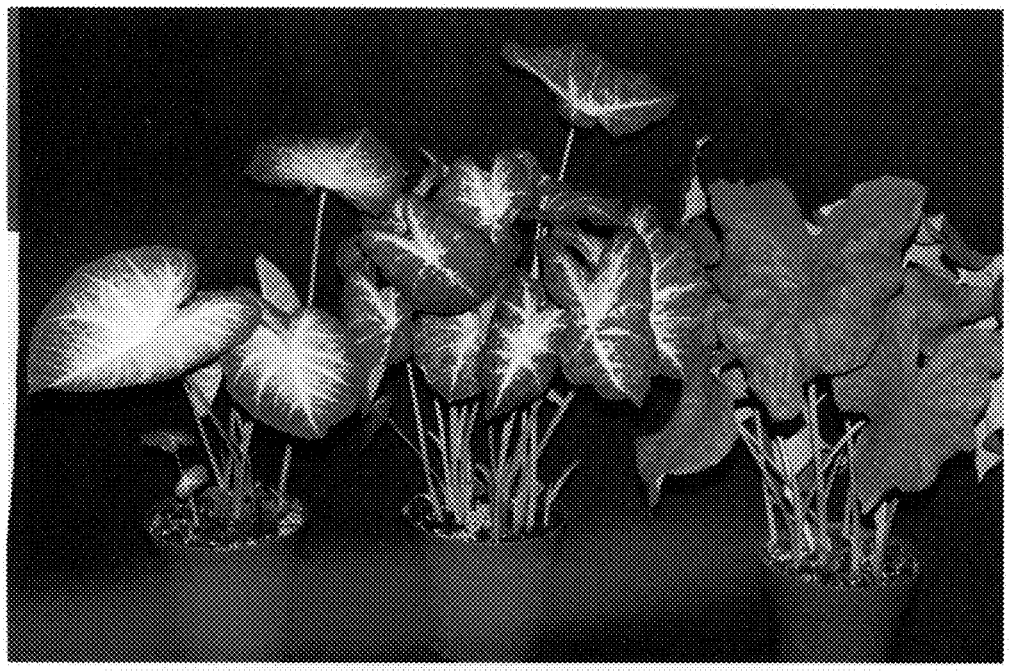
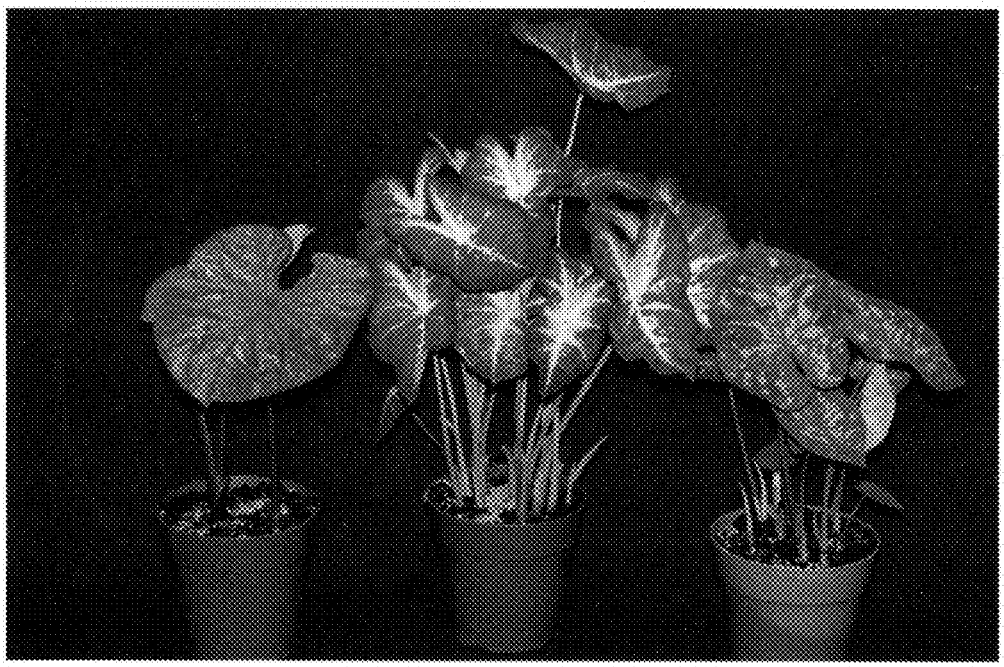

* * * * *